(12) United States Patent
Wendling et al.

(10) Patent No.: US 10,588,535 B2
(45) Date of Patent: Mar. 17, 2020

(54) METHOD OF CONSTRUCTING A DATA STRUCTURE REPRESENTATIVE OF A DYNAMIC REORGANIZATION OF A PLURALITY OF BRAIN NETWORKS, CORRESPONDING DEVICE AND PROGRAM

(71) Applicants: Universite De Rennes I, Rennes (FR); Institut Nationale de la Sante et de la Recherche Medicale, Paris (FR)

(72) Inventors: Fabrice Wendling, Rennes (FR); Mahmoud Hassan, Rennes (FR)

(73) Assignees: UNIVERSITE DE RENNES 1, Rennes (FR); INSTITUT NATIONALE DE LA SANTE ET DE LA RECHERCHE MEDICALE, Paris (FR)

( * ) Notice: Subject to any disclaimer, the term of this patent is extended or adjusted under 35 U.S.C. 154(b) by 122 days.

(21) Appl. No.: 15/743,511

(22) PCT Filed: Mar. 31, 2016

(86) PCT No.: PCT/EP2016/057140
§ 371 (c)(1),
(2) Date: Jan. 10, 2018

(87) PCT Pub. No.: WO2017/008926
PCT Pub. Date: Jan. 19, 2017

(65) Prior Publication Data
US 2018/0199848 A1   Jul. 19, 2018

(30) Foreign Application Priority Data

Jul. 10, 2015   (FR) ..................................... 15 56586

(51) Int. Cl.
*G06K 9/00* (2006.01)
*A61B 5/04* (2006.01)
(Continued)

(52) U.S. Cl.
CPC ...... *A61B 5/04842* (2013.01); *A61B 5/04012* (2013.01); *G06F 3/015* (2013.01);
(Continued)

(58) Field of Classification Search
None
See application file for complete search history.

(56) References Cited

U.S. PATENT DOCUMENTS

| 2013/0013030 A1* | 1/2013 | Mahadevan-Jansen ..................... A61N 5/0622 607/89 |
| 2013/0204114 A1* | 8/2013 | Huang ................. A61B 5/0476 600/409 |

OTHER PUBLICATIONS

English translation of the Written Opinion of the International Searching Authority dated Jun. 21, 2016 for corresponding International Application No. PCT/EP2016/057140, filed Mar. 31, 2016.
(Continued)

*Primary Examiner* — Idowu O Osifade
(74) *Attorney, Agent, or Firm* — David D. Brush; Westman, Champlin & Koehler, P.A.

(57) ABSTRACT

A method for determining a sequence of activation of a set of brain networks by an electronic device in the course of a predetermined cognitive task. The method includes: obtaining at least one time series of data on encephalographic activities, according to a predetermined sampling value, the data on activities representing a signal captured on the cranial surface by a capture device, during the execution of the predetermined cognitive task by at least one individual, delivering a set having at least one measurements vector per sample of the time series; for each measurements vector, determining connectivity between cortical sources, the cortical sources being obtained through measurements of a measurements vector, delivering a connectivity network; and grouping connectivity networks according to a resem-
(Continued)

Figure 1:
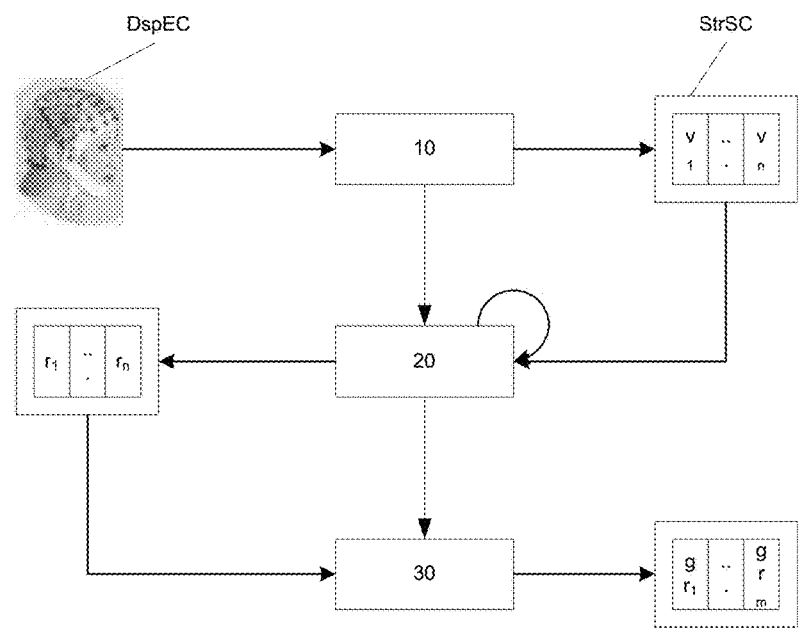

blance parameter delivering a set of groups of grouped connectivity networks, each representing an activity of a given brain network at a given instant.

8 Claims, 3 Drawing Sheets

(51) Int. Cl.
    *G06F 3/01*         (2006.01)
    *G06F 17/16*      (2006.01)
    *G06N 3/04*       (2006.01)
    *G06T 7/00*        (2017.01)
    *A61B 5/0484*     (2006.01)

(52) U.S. Cl.
    CPC ........... *G06F 17/16* (2013.01); *G06K 9/0057* (2013.01); *G06N 3/0454* (2013.01); *G06T 7/0016* (2013.01)

(56) References Cited

OTHER PUBLICATIONS

Bin He et al. "eConnectome: A MATLAB toolbox for mapping and imaging of brain functional connectivity". Journal of Neuroscience Methods, vol. 195., No. 2, pp. 261-269. Feb. 15, 2011.
Martin Billinger et al. "SCoT: a Python toolbox for EEG source connectivity". Frontiers in Neuroinformatics, vol. 8. Mar. 11, 2014.
International Search Report dated Jun. 21, 2016 for corresponding International Application No. PCT/EP2016/057140, filed Mar. 31, 2016.
Mahmoud Hassan et al., EEG Source Connectivity Analysis: From Dense Array Recordings to Brain Networks:, PLOS ONE, vol. 9, No. 8, Aug. 12, 2014 (Aug. 12, 2014), pp. e105041, XP55281987.
Mheich A. et al., "A new alogrithm for spartiotemporal analysis of brain functional connectivity", Journal of Neuroscience Methods, vol. 242, Jan. 10, 2015 (Jan. 10, 2015), pp. 77-81, XP029198221.
Written Opinion of the International Searching Authority dated Jun. 21, 2016 for corresponding International Application No. PCT/EP2016/057140, filed Mar. 31, 2016.

\* cited by examiner

METHOD OF CONSTRUCTING A DATA STRUCTURE REPRESENTATIVE OF A DYNAMIC REORGANIZATION OF A PLURALITY OF BRAIN NETWORKS, CORRESPONDING DEVICE AND PROGRAM

1. CROSS-REFERENCE TO RELATED APPLICATIONS

This Application is a Section 371 National Stage Application of International Application No. PCT/EP2016/057140, filed Mar. 31, 2016, the content of which is incorporated herein by reference in its entirety, and published as WO 2017/008926 on Jan. 19, 2017, not in English.

2. FIELD

The present technique relates to the field of medical imaging. The present technique relates more particularly to brain imaging. The term "brain imaging" designates all techniques derived from medical imaging that enable the observation of the brain, especially when an individual is carrying out a cognitive task. There are two big classes of brain imaging: structural imaging and functional imaging. The present technique relates to functional brain imaging, which seeks to perceive the functioning of the brain during the execution of a task, such as a cognitive task. This class of brain imaging can be used for example to locate the functional deficiencies of the workings of the brain.

3. PRIOR ART

It is a goal of functional imaging to model the brain in action. This class of imaging seeks to determine the functioning of the brain and can be of great use in determining cerebral functional disorders.

In the traditional use of functional brain imaging, an individual is made carry out a cognitive task and the signal produced by the brain activity is measured. Depending on the techniques and tools used, it is possible, with varying precision, to find that region of the brain that is particularly active at the instant when the cognitive task is performed. Classically used cognitive tasks include especially the task of picture naming.

Functional medical imaging is sub-divided into several types depending on the imaging technology used. We can cite here especially:
  imaging by functional magnetic resonance (fMRI) in which a signal known as a "BOLD" (blood-oxygen-level dependent) signal is measured, this signal reflecting the level of blood oxygenation in the brain;
  positron emission tomography (PET) in which the modifications of the blood flow are measured by means of a radioactive tracer: this tracer has to be preliminarily injected intravenously;
  electroencephalography (EEG) directly measures electrical activity on the cranial surface;
  magnetoencephalography (MEG) offers information relatively similar to that of EEG but measures the magnetic fields induced by cerebral activity.

Each of these techniques has advantages and drawbacks. Thus, for example, fMRI is considered to show low reactivity. Indeed, the technology used and the measurements carried out make it difficult to use this technique for measuring the rapid changes that take place in brain activity: with this technique, at best activity can be measured once per second. Now, it is known that the cognitive processes carried out are far more rapid. This means that this technique cannot be used to characterize rapid cognitive processes. Problems of the same order are encountered with PET: the diffusion of radioactive markers is relatively slow and it is difficult, with this technique, to access the dynamics of the cognitive processes. EEG for its part is considered to have low precision, especially because of a certain diffusion of the electrical signal on the cranial surface, which occurs independently of the number of electrodes used. MEG for its part offers better results in terms of precision for the locating of the signal-emitting sources. However, MEG requires heavy and bulky instrumentation that is not necessarily suited to every measurement situation. Indeed, unlike EEG, for which it is enough to have electrodes in order to measure the electrical signal, MEG requires a solenoid-fitted helmet which has the disadvantage of being bulky and requiring much space.

Apart from these problems of space requirement and precision, there are also problems of interpreting the results obtained. Indeed, depending on the imaging technique used, the results obtained are different, on the one hand because of the sampling of the measurements made (it will be understood that a one-second sampling operation for fMRI does not give results equivalent to 50 Hz or 100 Hz sampling) and, on the other hand, because of the interpretation of the results. More specifically, it appears that current imaging methods struggle to characterize the dynamics of information processing, especially during pre-determined cognitive tasks such as the picture-naming task.

There is therefore a need firstly to provide a brain imaging technique that is precise and simple in its application and the results of which precisely characterize the dynamics of information processing through the brain.

4. SUMMARY

The invention does not have the drawbacks of the prior art. In particular, the invention offers a solution that is precise, economical and at the same time can be used to characterize information processing, for example in the context of a picture-naming task.

More specifically, the present invention relates to a method for determining a sequence of activation of a set of cerebral or brain networks, in the course of a predetermined cognitive task, a method applied using an electronic device comprising means for obtaining data on encephalographic activities.

Such a method comprises:
  a step for obtaining at least one time series of data on encephalographic activities, according to a predetermined sampling value, said data on activities representing a signal captured on the cranial surface by means of a capture device, during the execution of said predetermined cognitive task by at least one individual, a step delivering a set comprising at least one measurements vector per sample of the time series;
  for each measurements vector, a step for determining a connectivity between cortical sources, said cortical sources being obtained through measurements of a measurements vector, delivering a connectivity network;
  a step for grouping connectivity networks according to a resemblance parameter delivering a set of groups of grouped connectivity networks, each representing an activity of a given brain network at a given instant.

According to one general characteristic, said step for obtaining a time series comprises:
- a plurality of steps for obtaining a plurality of values of signals captured at the cranial surface of said at least one individual, said plurality of values representing a number of signal capture devices, said plurality of steps for obtaining these pluralities of values depending on a duration of said predetermined cognitive task and of said predetermined sampling;
- a plurality of steps for associating said value with a given cortical source, delivering said set comprising at least one source vector per sample.

According to one particular embodiment, the number of signal capture devices is greater than 128.

According to one particular embodiment, said sampling value ranges from 0.2 ms to 30 ms.

According to one particular characteristic, said step for determining connectivity between cortical sources of a vector comprises:
- a step for detecting sources from which the signals of said vector have come, said step for detecting implementing a weighted minimum norm estimation (wNME), delivering a source vector;
- a step for computing a functional connectivity between the previously detected sources, by means of a method of phase synchronization (PS), delivering a connectivity network for the source vector.

According to one particular characteristic, said step for grouping connectivity networks according to a resemblance parameter comprising at least one iteration of the following steps:
- selecting a predetermined number K of networks from among the set of connectivity networks;
- computing, for each network among the number K of previously selected networks, a spatial correlation between this network and the set of connectivity networks;
- selecting the network for which the spatial correlation is the highest and allocating, to this network, the spatially closest networks.

According to another aspect, the invention also relates to an electronic device for determining a sequence of activation of a set of brain networks, during a predetermined cognitive task, the electronic device comprising means for obtaining data on encephalographic activities.

Such a device comprises:
- means for obtaining at least one time series of data on encephalographic activities, according to a predetermined sampling value, said data on activity representing a signal captured on the cranial surface by at least one capture device during the execution of said predetermined cognitive task by at least one individual, the step delivering a set comprising at least one measurements vector per sample of the time series;
- means for determining a connectivity between cortical sources for each measurement vector, said cortical sources being obtained from measurements of a measurement vector, delivering a connectivity network;
- means for grouping connectivity networks according to a resemblance parameter delivering a set of groups of grouped connectivity networks, each being representative, at a given point in time, of an activity of a given brain network.

According to one specific implementation, the different steps of the method according to the invention are implemented by one or more software programs or computer programs comprising software instructions that are to be executed by a processor of an information-processing device, such as a terminal according to the invention and being designed to command the execution of the different steps of the methods.

The invention is therefore also aimed at providing a computer program, capable of being executed by a computer or by a data processor, this program comprising instructions to command the execution of the steps of a method as mentioned here above.

This program can use any programming language whatsoever and be in the form of source code, object code or intermediate code between source code and object code such as in a partially compiled form or in any other desirable form whatsoever.

The invention is also aimed at providing an information carrier readable by a data processor and comprising instructions of a program as mentioned here above.

The information carrier can be any entity or communications terminal whatsoever capable of storing the program. For example, the carrier can comprise a storage means such as a ROM, for example, a CD ROM or microelectronic circuit ROM or again a magnetic recording means, for example a floppy disk or a hard disk drive.

Furthermore, the information carrier can be a transmissible carrier such as an electrical or optical signal that can be conveyed via an electrical or optical cable, by radio or by other means. The program according to the proposed technique can especially be uploaded to an Internet type network.

As an alternative, the information carrier can be an integrated circuit into which the program is incorporated, the circuit being adapted to executing or to being used in the execution of the method in question.

According to one embodiment, the proposed technique is implemented by means of software and/or hardware components. In this respect, the term "module" can correspond in this document equally well to a software component and to a hardware component or to a set of hardware and software components.

A software component corresponds to one or more software module programs, one or more sub-programs of a program or more generally to any element of a program or a piece of software capable of implementing a function or a set of functions according to what is described here below for the module concerned. Such a software component is executed by a data processor of a physical entity (terminal, server, gateway, router etc) and is capable of accessing hardware resources of this physical entity (memories, recording media, communications buses, input/output electronic boards, user interfaces etc).

In the same way, a hardware component corresponds to any element of a hardware assembly capable of implementing a function or a set of functions according to what is described here below for the module concerned. It can be a programmable hardware component or a component with an integrated processor for the execution of software, for example, an integrated circuit, a smart card, a memory card, an electronic board for the execution of firmware etc.

Each component of the system described here above can of course implement its own software modules.

The different embodiments mentioned here above can be combined with one another to implement the proposed technique.

5. FIGURES

Figure 2:
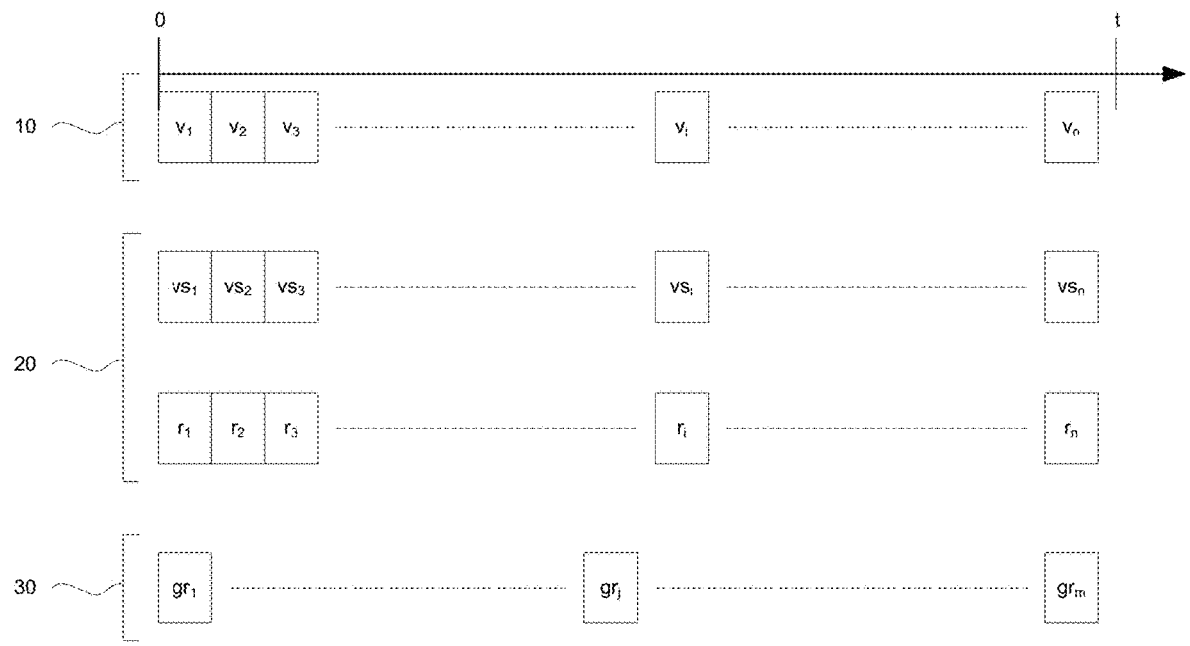
Figure 3A:
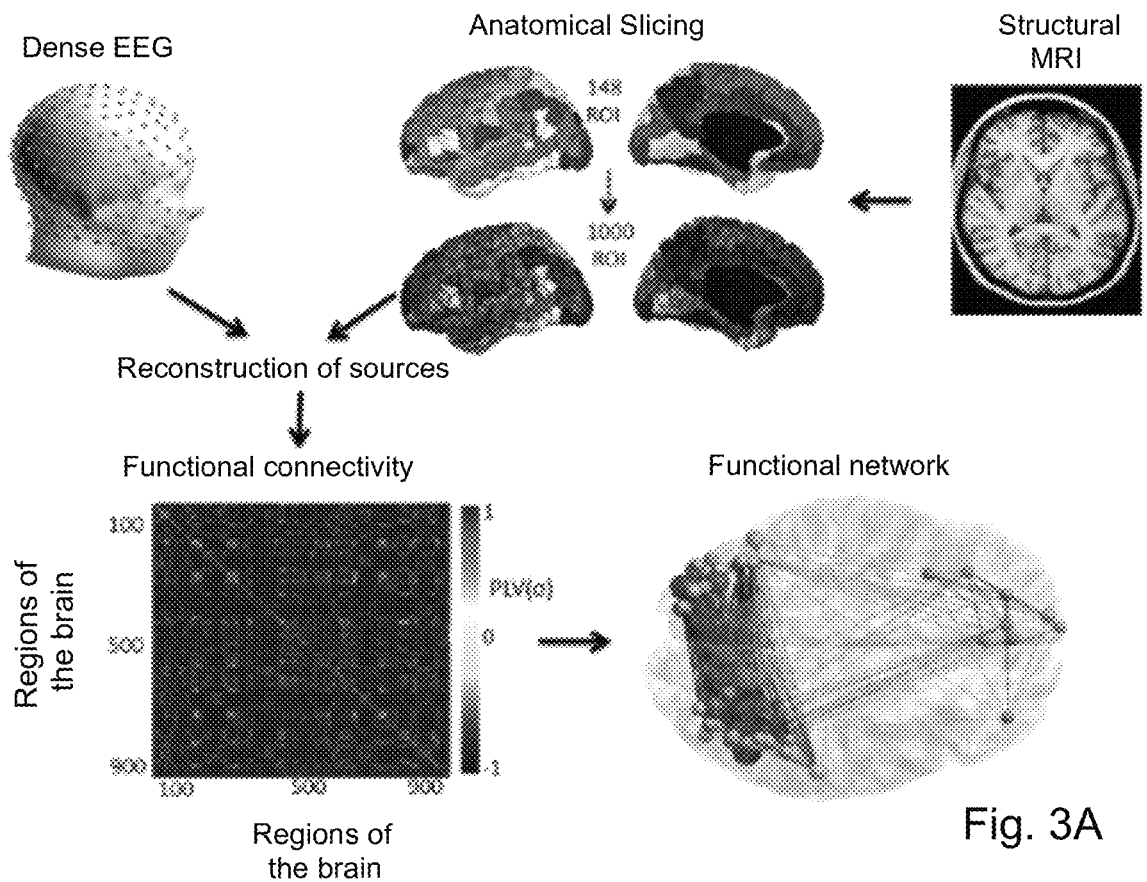
Figure 3B:
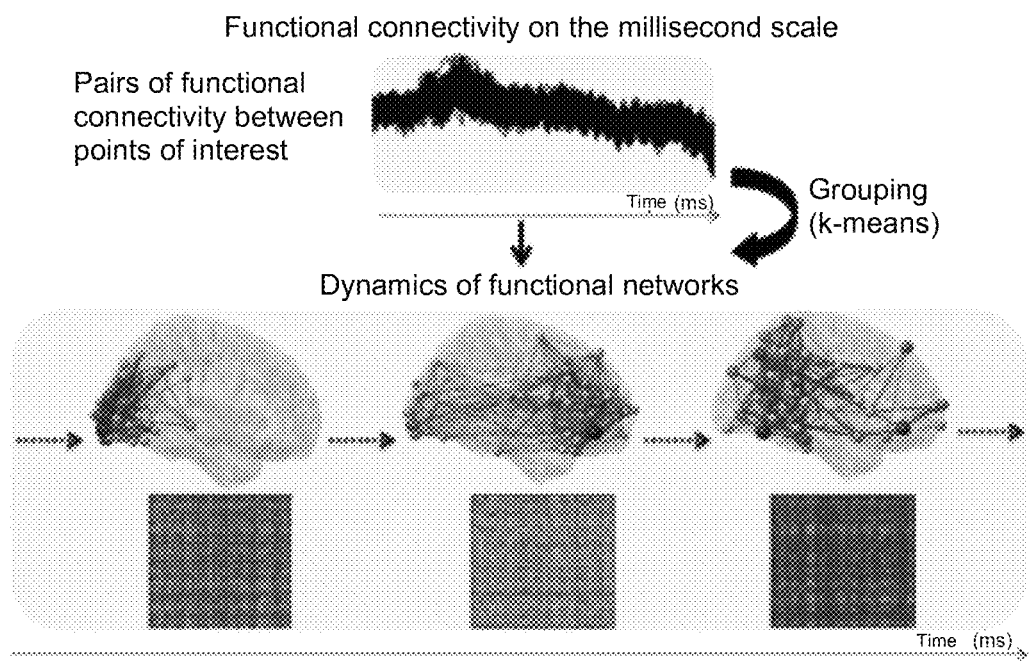
Figure 4:
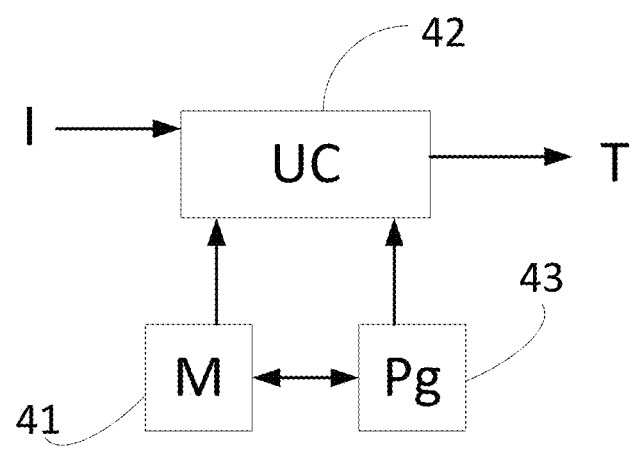

Other features and advantages of the invention shall appear more clearly from the following description of a preferred embodiment, given by way of a simple illustrative and non-exhaustive example and from the appended drawings, of which:

FIG. 1 is a block diagram of the proposed technique;

FIG. 2 briefly describes the data implemented in the present technique;

FIGS. 3A and 3B describe an embodiment in the case of dense electroencephalograms;

FIG. 4 describes a device such as a brain-imaging device capable of implementing a resource according to the present technique.

6. DESCRIPTION

6.1. Reminder of the Principle

For efficient processing of the information during cognitive activity, the functional brain networks must get rapidly and dynamically organized within a time scale of less than one second. The question of tracking of the spatio-temporal dynamics of large-scale networks over this short duration is a very difficult one.

Indeed, any cognitive process implies the activation of a large-scale functional brain network. In the processes of vision, attention and memory, this network is characterized by an increase in the synchronization of the cortical oscillations (in the gamma frequency range especially but not solely in this range) through sets of distant neurons distributed over distinct areas of the brain.

The precise tracking of the spatio-temporal dynamics of large-scale networks during the time of the cognitive processes (often as short as some hundreds of milliseconds) is difficult. A certain number of theories have been elaborated to explain these spatio-temporal dynamics. It has been hypothesized that a functional brain network makes rapid transitions between transiently stable states, each being characterized by a network with an intrinsic dynamic and specific functional relationships between the sets of neurons. According to this theory, the substrate of cognitive processes should correspond to a sequence of switches between the networks and therefore to time-dependent and space-dependent fluctuations in the node and arc properties of the total network.

The validation of these hypotheses for task-related data requires tracking of the brain processes on a time scale of the order of one millisecond. This can hardly be done using fMRI data for a simple and well-known reason: even if the BOLD signals are characterized by excellent spatial resolution, they reflect the metabolic and hemodynamic response of sets of neurons (at the voxel level). This slow response (in seconds) is clearly linked to the high-speed dynamics of the cortical oscillations that take place over interconnected sets of neurons and that define functional networks, but do so indirectly (i.e. through neuro-glio-vascular coupling).

The present invention approaches this problem by using high spatial resolution electroencephalography (EEG), for example recorded during a picture-naming task. Using a specific method, described here below, we determine the dynamics of the networks successively implemented for carrying out the cognitive task. The general principle of the invention is presented with reference to FIGS. 1 and 2. FIG. 1 represents the method in a general way and FIG. 2 represents the data handled.

Thus, the invention relates to a method and a device for obtaining a piece of data representing an activation of at least one brain network activated during a predetermined task, method comprising the following steps:

obtaining (10) a data structure representing activation of cortical sources (StrSC); this data corresponding to signals, captured by an extra-cranial device (DspEC), placed on the individual's cranium: this may be an electrode helmet for EEG or a magnetoencephalogram; at a given point in time, a general measurement, represented by a measurement vector $(v_1, v_2, v_3, \ldots v_i, \ldots v_n)$, representing a set of signals sent (signal vectors) is obtained; the frequency with which these sent signals (i.e. the number of vectors) are obtained depends on the measurement device on the one hand and on the time (t) needed to carry out the task on the other hand;

in a measurement vector (or signals vector), there are as many signal measurements as there are electrodes: if for example a measurement is made with 256 electrodes, there are 256 values available in the measurements vector.

determining (20) a connectivity between the sources of a same network: for each vector $(v_1, v_2, v_3, \ldots v_i, \ldots V_n)$, that represents a network, it is sought to determine the connectivity of the different components of the vector with one another; in other words, it is sought to measure the interaction of one component of the vector with other components of the vector in order to determine whether these components are related with one another; at the end of this phase, a connectivity network $(r_1, r_2, r_3, \ldots r_i, \ldots r_n)$, is obtained, which for the period of time considered is considered to be active;

in a sources vector (i.e. a connectivity network), there are not necessarily 256 sources available; as explained here below, the sources vector comprises phase values associated with the sources of the perceived signal and not with the capture device (electrodes): the number of sources is therefore in principle different from the number of capture devices; thus, to determine the connectivity, a first computation consists in estimating the sources from the signals; the sources represent finally the points or regions of interest (ROI);

the connectivity network is obtained (computed) from the sources and not from the signal (i.e. the connectivity network is computed not directly from the measurement vector but from the intermediate sources vector);

grouping (30) the connectivity networks $(r_1, r_2, r_3, \ldots r_i, \ldots r_n)$ with one another according to their resemblance delivering groups of connectivity networks $(gr_1, gr_2, gr_3, \ldots gr_j, \ldots gr_m)$.

The frequency with which, for a given subject, data structures representing cortical sources are obtained depends firstly on the device that enables this data to be obtained and secondly on the predetermined cognitive task. For example, for a picture-naming task, the frequency ranges from 1 ms to 30 ms. For a task of listening to a sound, the frequency can be different, for example from 0.2 ms to 1 ms. The successively obtained data structures $(v_1, v_2, v_3, \ldots v_i, \ldots v_n)$ can be grouped together in a single data structure (StrSC) that contains all the data obtained during the performance of the task by the subject. Thus, in a particular embodiment, the data can be stored in a table or a matrix, one of the dimensions of which relates to the number of samples while the other dimension includes the number of measurements made for one sample.

For example, when a cognitive task lasts one second and when a one-millisecond sampling is done, 1000 signal vectors are obtained: there are therefore 1000 data structures representing successive operations for activating cortical sources.

For each of these structures, a step is performed for determining connectivity between the sources, this step delivering, for each structure, a network determined at an instant t which is the instant considered by the original vector. At the end of the determining of the connectivity, therefore, 1000 networks are obtained (considering the previous example of a 1-second cognitive task sampled at 1 ms).

Determining the connectivity between the sources can include complementary data-processing steps depending on the goal to be attained and the number of subjects involved.

Thus, when it is sought to carry out a statistical study on a large number of subjects, then in order to eliminate bias, it is appropriate to take the average of the different results (i.e. the different networks) obtained from all the subjects. Returning to the previous example, if it is assumed that the cognitive task is performed by 20 subjects, each subject "produces" 1000 connectivity networks (for a 1-second task sampled every millisecond). It is then appropriate to take the average of the networks obtained. This is done by taking an average of the networks at the time t considered: an average is taken of the first 20 networks at 1 ms and then an average of the next 20 networks at 2 ms, etc. until the average is taken for all the networks of the 20 subjects of the statistical study. At the end, we therefore obtain 1000 networks, each of these 1000 networks representing an average for the 20 subjects of the statistical study.

On the contrary, when the measurement relates to only one subject, for example in order to determine the behavior of this subject relative to a pre-determined statistical atlas (i.e. the atlas obtained following the application of the first case, for example), the networks do not need to be modified. At the very most, the average can be taken of the results for this single subject: if the subject to be studied has carried out ten similar cognitive tasks (for example ten cognitive tasks for naming an object: a cup, a watch, glasses, a pencil, a map, keys, computer, bottle, spoon, sheet, etc.), it can be planned to take the average of the networks corresponding to these ten tasks which in principle make use of the same networks and the same transitions. In this case, the computation of the average is substantially identical to that made in the context of 20 subjects and a single task.

The next operation consists in grouping together these networks, by resemblance. The purpose of this grouping is not trivial: it makes it possible to obtain an essential piece of information (often missing or imprecise) on current techniques (especially those based on EEG or MEG) i.e. to determine, in time, the different networks activated and the transitions between these networks. The different networks activated and their transitions represent the cortical zones implemented and the interaction of these cortical zones with each other to carry out the given cognitive task.

In other words, the analysis of connectivity of the EEG sources is used to track the spatio-temporal dynamics of large-scale networks associated with cognitive activity. To this end, for example high spatial resolution EEG data are collected during the application of the picture-naming task. The functional networks are reconstructed in both their space and time dimensions, throughout the duration of the cognitive process (on the basis of the perception of the image up to the motor response) by using a method that combines i) the solution of the inverse EEG problem, ii) the estimating of brain connectivity on the basis of phase-locking values and iii) the segmenting of the functional networks by using a clustering method. FIG. 3 provides a brief description of the application of the present technique in the case of high density EEG: A) dense EEGs (256 electrodes) are recorded during the picture-naming task. The structural MRI images are segmented and subjected to anatomical parcellation for example by using the Freesurfer software to obtain 148 regions. These 148 regions are sub-divided by using Brainstorm to obtain a higher spatial resolution (about 1000 regions of interest). The inverse problem is resolved by using the weighted minimum normal estimation algorithm. The time series of the reconstructed sources are obtained. The functional connectivity between the reconstructed sources is computed by using the phase-locking value method. A high-resolution functional connectivity matrix is obtained and the corresponding functional brain network is viewed. B) This procedure is carried out on the one-millisecond scale and a large number of functional connectivity matrices are obtained. A k-means approach is used to obtain the brain network states (BNS) by using, for example, a segmentation algorithm described in detail here below in the present document.

6.2. Obtaining a Data Structure Representing the Activation of Cortical Sources

In this embodiment, the brain activity is recorded by means of a high spatial resolution EEG system, using 256 electrodes (from Electrical Geodesic Inc. (EGI)). The main characteristic of this system is the large coverage of the subject's head by surface electrodes that improve the analysis of the intra-cerebral activity, using non-invasive measurements obtained on the scalp, as compared with standard systems using 32 to 128 electrodes. The EEG signals are acquired at a sampling frequency of 1 kHz and the bandpass filter is defined between 3 Hz and 45 Hz. Thus, in this embodiment, the size of a vector is 256 including therefore 256 signal values. A piece of data of the vector is spatially located (this is the place where the electrode is positioned) and possesses a signal value.

It can be noted that, in this embodiment, high spatial resolution EEG is used. It is quite possible to envisage the use of other methods for obtaining data, the important point being that this data should be present. Thus, MEG can also be used as well as other methods.

6.3. Determining the Connectivity of the EEG Sources for Each Vector

As indicated here above, for each basic data vector, a search is made to determine the presence of a network. To this end, a computation is carried out to determine connectivity between the sources of a same vector. In other words, it is sought to verify that such or such a vector value is associated with such or such other vector value by a predetermined relationship. This is done by computing the synchronization of phases between these two vectors.

A crucial step when carrying out the analysis of connectivity of the EEG sources is the choice of three factors: the method used to resolve the inverse problem, the method used to compute functional connectivity between the time series of the reconstructed sources and the number of measurements (for example the number of electrodes used on the scalp in the present case). Very recently, a comparative study of these factors was made. It appears that the combination of the weighted minimum norm estimation (wMNE) with the phase locking value (PLV) made by using high-resolution EEG is the best among the combinations tested. This combination is used in the present invention.

Thus, to obtain connectivity networks, we implement:
- a step for constructing sources from values of signals measured during the cognitive task by using the weighted minimum norm estimation (wMNE);
- a step for computing the functional connectivity between the reconstructed sources by means of the phase synchronization (PS) method.

6.3.1. Reconstruction of the Sources

According to the linear discrete equivalent current dipole model, the EEG signals S(t) measured from the Q channels can be expressed by linear combinations of time-varying dipole sources D(t):

$$S = G \cdot D + B$$

where G and B(t) are respectively the matrix containing the lead fields of the dipole sources and the added noise. In general, the inverse problem consists in finding an estimation of $\hat{D}(t)$ of the parameters of the dipole sources (generally, the position, orientation and amplitude), given the EEG signals S(t) and taking account of the gain matrix G. This matrix can be computed from a multilayer head model (volume conductor) and from the position of the electrodes. For example, the finite boundary elements method is a numerical method traditionally used in the case of realistic head models.

Since this problem is ill-stated (P>>Q), physical and mathematical constraints must be added to obtain a unique solution among the numerous solutions that minimize the residual term in the organization of the measured EEG signals. Using segmented MRI data, the distribution of the sources can be limited to a field of current dipoles homogenously distributed on the cortex, and normal to the cortical surface.

Technically, in the source model, it is assumed that the EEG signals are generated by pyramidal cell macro-columns situated in the cortical mantle and orthogonally aligned with the surface. Thus, the electrical contribution of each macro-column to the electrodes on the scalp can be represented by a current dipole located at the center of gravity of each triangle of the 3D mesh and oriented normally to the surface of the triangle. In using this source space, the weighted minimum normal estimation method can be used to estimate only the moments of the dipole sources. The wMNE method compensates for the tendency of the traditional minimum normal estimation (MNE) method to favor sources that are weak and on the surface. This is done by introducing a weighting matrix $W_S$:

$$\hat{D}_{wMNE} = (G^T W_S G + \lambda I)^{-1} G^T W_S S$$

where the matrix $W_S$ adjusts the properties of the solution by reducing the bias inherent in minimum normal estimation (MNE) solutions. Classically, $W_S$ is a diagonal matrix built from the matrix G with non-zero terms inversely proportional to the norm of the lead field vectors. The value of $\lambda$ is computed relative to the signal-to-noise ratio for each signal computed as the ratio between the post-stimuli period and the pre-stimulus period (200 ms). The value $\lambda$ ranges from 0.1 to 0.3.

The sources are reconstructed for each trial (same number of sources for each trial) and the functional connectivity is then computed between the reconstructed sources by means of the phase synchronization method (PS).

6.3.2. Computation of Functional Connectivity

The first step for estimating the phase synchronization (PS) is to extract the instantaneous phase of each signal. To this end, the invention uses the method based on the Hilbert transform.

The second step is the definition of an appropriate index to measure the degree of synchronization between the estimated instantaneous phases. To measure the phase synchronization (PS) a phase locking value (PLV) method is used. For each pair of sources, x and y, at the instant t ($t = t_1, \ldots, t_T$ where $T = D^* f_s$; D and $f_s$ designate the signal length relative to the appearance and to the sampling frequency respectively) for the trials Tr and for the subject j (j=1 . . . M, where M designates the number of subjects), the phase locking value (PLV) is defined by:

$$PLV_{xy}^j(t) = \frac{1}{Tr} \left| \sum_{n=1}^{N} \varphi_x(t) - \varphi_y(t) \right|$$

To reduce the effect of the correlations between the approximate electrodes, a standardization procedure (score z) is applied so that the values $PLV_{xy}$ are compared with the 200 ms baseline preceding the presentation of the image. Let $\mu_{xy}$ and $\sigma_{xy}$ be the mean and standard deviation computed from a 200 ms baseline. The normalized phase locking values (PLV) are then defined by:

$$\overline{PLV}_{xy}^j(t) = (PLV_{xy}^j(t) - \mu_{xy}^j)/\sigma_{xy}^j.$$

The functional connectivity is computed in the low gamma frequency band (30 to 45 Hz). This frequency band is the one most relevant in the context of the cognitive task performed, namely the object-naming task. Other cognitive tasks could necessitate a computation of functional connectivity in other frequency bands. This however would in no way detract from the general computation method as proposed.

Following this step, the functional connectivity is determined for each of the original vectors, and connectivity networks are available. Returning to the previous example, for a given subject, at the end of this step there are 1000 individual connectivity networks available, networks that will be sought thereafter for grouping together, in order to determine periods of activation and transition between these networks throughout the cognitive task (this is the segmentation algorithm).

6.3.3. Average of the Functional Connectivities

However, before carrying out the segmentation, there are possibilities of additional processing of the data obtained, as mentioned here above, depending on the goal pursued and the number of subjects involved.

Thus, in the event of a "multiple subject" application, with the aim of carrying out a statistical study, the phase locking values (PLV) are then averaged for all the subjects:

$$\overline{PLV}_{xy}(t) = \frac{1}{M} \sum_{j=1}^{M} PLV_{xy}^j(t)$$

where $\overline{PLV}_{xy}(t)$ represents the general term of the average connectivity matrix $\overline{PLV}(t)$ which defines a functional connectivity network N at each instant t, $N = \{N(t), t=1, \ldots, T\}$, computed for the V pairs of x and y, where V is equal to ($Nc \cdot (Nc-1)/2$)) and Nc is the number of regions of interest (ROI).

6.4. Determining Brain Network States—Implementation of Grouping Together (Applying a Segmentation Algorithm).

To carry out this step, in this embodiment, the invention implements an algorithm for breaking down a cognitive task into brain network states (BNS) characterized by significantly high functional connectivity values in a sufficiently long time window.

The goal of this algorithm is to identify clusters among the T networks N(t). The proposed algorithm is based on the k-means clustering of the connectivity networks obtained by the phase locking value (PLV) method presented here above. This approach summarizes the brain networks in a limited number of dominant networks over a given period of time.

In general, the process for determining brain network states is based on connectivity networks (represented by connectivity matrices) previously obtained (and averaged when the data from several subjects are taken into account).

K networks (varying from 3 to 12) are randomly selected and spatial correlations are computed between the previously selected K networks and all the other T networks (the remaining networks). A spatial correlation value is obtained for each value K at each interval and for any unspecified one of the T networks, only one of the K networks produces the highest spatial correlation. Ultimately, the cross-validation criterion is used to determine the optimum number of networks that best explains the cognitive task in progress.

When several subjects participate in the statistical study, to study the variability between the subjects, the invention adds an index called a "network presence" index used to compute the ratio (in %) of the networks/clusters identified among all the subjects.

The segmentation algorithm is described here in greater detail in the case of an applicability to a group of subjects. It is quite applicable to data that comes from only one subject.

The goal of this algorithm is to identify clusters among T networks N(t). The proposed algorithm is based on three main steps:

1. Initialization

To begin with, K networks $N^k$, $N^k = \{\overline{N^k}, k=t_1, \ldots, t_K\}$, are selected wherein $k=t_i$ and i is selected randomly in [1,T] (K varies from 3 to 12 and k varies from 1 to K).

2. Allocation

The spatial correlation $C^k(t)$ between N(t) and $\overline{N^k}$ is then computed as follows:

$$C^k(t) = \frac{\sum_{i=1}^{V} \overline{N_i^k} \cdot N_i(t)}{\sqrt{\sum_{i=1}^{V} \overline{N_i^k}^2} \cdot \sqrt{\sum_{i=1}^{V} N_i^2(t)}} \quad (1)$$

Where i designates the $i^{th}$ edge in N(t) and $\overline{N^k}$. As represented in the equation 1, C is standardized by the variance of the networks N and $N^k$. Thus, C ranges from 0 to 1. High values indicate networks having high similarity. Conversely, low values indicate a low similarity between the networks.

Each network N(t) is then allocated to the cluster for which the spatial correlation is the highest. The allocated clusters are defined by $\hat{N}^k$:

$$\hat{N}^k = \left\{ N(t) : C^k_{N(t),\overline{N^k}} \geq C^{k'}_{N(t),\overline{N^{k'}}} \forall 1 \leq k' \leq K \right\} \quad (2)$$

From these values of spatial correlation, the overall variance (GV) is computed as such:

$$GV = \sum_{k=1}^{K} GV^k \quad (3)$$

$$GV^k = \sum_{t=1}^{tmax} \left( C_{N(t),\overline{N^k}} \right)^2 \cdot \gamma_{N(t),\hat{N}^k} \quad \text{où} \quad \gamma_{N(t),\hat{N}^k} = \begin{cases} 1 & \text{if } N(t) \in \hat{N}^k \\ 0 & \text{if } N(t) \notin \hat{N}^k \end{cases} \quad (4)$$

3. Updating

At each iteration, the new centroids $\overline{N^k}$ are updated by computing the average for all the networks giving the same cluster.

$$\overline{N^k} = \frac{1}{|\hat{N}^k|} \sum_{N' \in \hat{N}^k} N' \quad (5)$$

For each value K, the steps 1 and 3 are repeated 500 times. The set of centroids leading to the highest global variance (GV) is selected. When the algorithm converges (attaining the highest global variance)), the networks K+1 $\overline{N}$ are then selected randomly and the entire procedure here above (from the step 2 to the step 3) is repeated until K=12.

To select the optimum number of clusters, we have used a method based on the cross-validation (CV) criterion which is a ratio between the global variance (GV) and the degrees of freedom for a given set of graphs. As indicated, the global minimum of this criterion gives the optimum number of segments.

Finally, the above-described method is a group-averaged approach, which means that this method is based on the computation of the spatial correlation between the networks on averaged $\overline{PLV}(t)$ adjacency or proximity matrices obtained from all the subjects. However, the algorithm does not overlook the inter-subject variability. To analyze the single-subject contribution, the same type of computation (mainly the step 2) can be performed between the single-subject $PLV^j(t)$ and the clusters obtained by the clustering algorithm applied to $\overline{PLV}(t)$. In this case too, each time point is marked according to the graph with which it is best correlated, giving a measurement of the "network presence". This procedure is particularly useful for analyzing, extracting and identifying spatio-temporal behaviors that are common across subjects.

6.5. Other Features and Advantages 6.5.1. Statistical Tests

The segmentation algorithm based on k-means produces a certain number of functional connectivity states (clusters). It is assumed that these clusters reflect changes in the cognitive state. To verify this hypothesis, our results are compared with an appropriate null model. The identified clusters are compared with those obtained by shuffling the original data in using surrogates. In brief, the invention uses multivariate Fourier transform surrogates ($n_{sur}=1000$) generated from original EEG data for all the trials. These substitutes correspond to states of realization of linear stationary processes with preserved characteristics of automatic and cross correlation. The same processing steps are performed on these surrogates as those made on the original data: filtering in the 30 to 45 Hz gamma frequency band, computing functional connectivity by using a phase locking values method in this frequency band, thresholding of the connectivity matrices and segmentation into clusters using the k-means algorithm. The spatial distributions (Sd) and the temporal profiles (Tp) of the original clusters are compared with those obtained in using surrogates.

With regard to Tp, when a cluster is significant (i.e. linked to the cognitive process and not to chance), the value of Tp for the surrogate data ($Tp_{surr}$) will be different from that of the original cluster ($Tp_{org}$). The underlying null hypothesis is that the clusters obtained are significantly different from the spurious network states that can always be seen in random data or white noise. The null hypothesis is tested by comparing $Tp_{surr}$ and $Tp_{org}$ by means of a statistical test. The "rank test" is used to reject or accept the null hypothesis. Basically, [$Tp_{org}$; $Tp_{surr}$] is sorted out in rising order and the rank index for $Tp_{org}$ is returned. With a certain number of surrogates (n_surr=1000 for example), if this rank is >990 and <10 (significance level at 99%), this means that it is in the distribution tail-end and that the null hypothesis can be rejected (two-tail test) with a significance of p=2*(1/(n_surr+1))=0.002. A similar test is used for the spatial distributions (Sd). For multiple tests and to take charge of the familywise error rate (FWER), the Bonferroni correction test is used, this method being considered to be the simplest and most conservative method to control the FWER problem.

6.5.2. Regions of Interest and Network Measurements

Freesurfer is used to register a labelled mesh from an average brain, where each label corresponds to one of 148 anatomical cortical regions. This output gave a standardized division of the cortex into 148 regional areas. Each of these areas was then sub-divided into a set of small sub-regions using Brainstorm, giving 1000 regions of interest (ROI) covering the entire cortex. This segmentation gives high-resolution connection matrices. These regions of interest (ROI) were then take into account in order to obtain a non-directed, weighted, sparse graph, the thresholds of the adjacency matrices being determined. For each matrix, 10,000 edges were selected. All the corresponding values of weight were positive. Then, the strength measurement is used to characterize the nodes in the weighted networks obtained. This measurement is defined by the sum of all the arc weights for each node. For any unspecified node i, the resistance $k_i^w$ is defined by:

$$k_i^w = \sum_{j \in N} W_{ij}$$

where N is the set of all the nodes in the graph and $W_{ij}$ is the connection weight between two nodes i and j.

6.5.3. Other Methodological Characteristics

The appropriate processing of the dense EEG reveals the spatio-temporal dynamics of the functional brain networks.

The technique presented here above is used to characterize the spatio-temporal dynamics of the brain networks for a short-term (<1 second) cognitive task using EEG data obtained on the scalp. The results show that the appropriate processing of the high spatial resolution EEG recordings can be used to identify the networks that are in tune with the regions of the brain involved in the same cognitive task and identified through other modalities (mainly fMRI and PET). However, these results go beyond those obtained with classic neuro-imaging techniques because the proposed method offers the unique advantage of tracking the dynamics of the network at high temporal resolution (of the order of 1 ms) and spatial resolution (~1000 regions of interest (ROI)).

The high performance of this processing operation can be explained by the three steps used to obtain networks relevant in terms of time and space characteristics. The first step is the reconstruction of cortical sources distributed in a high-resolution mesh in resolving the inverse EEG problem. The second step is the estimation of the functional connectivity by using the phase synchronization between the gamma oscillations present in the development, over time, of the reconstructed sources. The results show that this step is crucial for identifying networks having high specificity with respect to the task performed. A multi-factor analysis is carried out beforehand to examine the effect of the different factors that come into play in the analysis of connectivity of the EEG sources. This methodological study has shown that the wMNE algorithm associated with the phase locking value using a dense network of electrodes (180 electrodes on the scalp) gives optimal results. The third step is the segmentation, in time, of the cognitive process into brain network states (BNS). On the basis of the k-means clustering of the brain networks on the 1 ms scale, an algorithm is implemented, applied initially to scalp EEG. This algorithm is used for the first time on the networks at the cortical level. This segmentation procedure automatically leads to a timing that heavily corresponds to the successive steps previously related to brain processing from image perception up to naming of sound. This "switching behavior" of the functional connectivity networks has been very recently reported for data on resting states using a modelling approach.

Functional Connectivity of the Sources Relative to the Location of the Sources

A major question dealt with in the present document relates to the difference between the proposed network-based approach and the previously used approach seeking to locate the sources of regions activated during cognitive tasks. Although these two (source-based and network-based) networks) give similar results for certain networks, this is not the case for others.

From the conceptual viewpoint, the fundamental difference between the two approaches is that the source location approach totally ignores all possible interactions between the regions of the brain. When the location of the sources is analyzed, the sources having the highest amplitude (averaged at the given period or computed at the instant of peak amplitude of the signal) are traditionally selected. However, to a certain extent (depending on the threshold), this approach overlooks the possible contribution of "low energy" sources. The thresholding process can considerably modify the results of the location. For example, when only the sources having the highest amplitudes of 50% to 75% are maintained in the wMNE algorithm, the temporal lobe is not selected as being active even though it has been stated that it participates in semantic processing in exactly the same task.

Conversely, the hypothesis on which the network-based approach is based is that the sources can be synchronized independently of their amplitude. The results show that the edges represented in the networks identified correspond to connections both among sources having high amplitude (occipital connections) and sources having low amplitude (temporal lobes). Thus, the network-based approach reveals networks that are more specific to the task performed. One example that is illustratory is the absence of the dorso-lateral prefrontal cortex in networks identified during the first 200 ms while this region is particularly active throughout the duration of the task in the source-location approach, probably because of sustained attention processes that are not particularly related to visualization, decoding and picture-naming.

Methodological Considerations

In the present document, for at least one embodiment, the entire processing operation is performed on mean data of a group of subjects (and not of a unique subject). The connectivity matrix is computed by using the phase locking value (PLV) method at each time interval for each subject and all the matrices are averaged for all the subjects of the group, giving an average connectivity matrix of the group at each time sample of the post-stimulus response. The segmentation algorithm is applied to this average data. The main advantage of this approach is that it preserves the networks common to all the subjects of the group and reduces inter-individual variability. The results obtained from this analysis therefore represent the spatio-temporal dynamics of the networks that occur most constantly within the group of subjects. It is also interesting to note that it is assumed i) that there is an anatomical correspondence among subjects (a 3D mesh model is used as the source model) and ii) that the transitions between the functional connectivity states occur in a repeatable manner among subjects. However, inter-subject variability has not been totally overlooked. The "network presence" index of each brain network state (BNS) is computed among all the subjects. The results show that the first three brain network states (BNS) have the highest network presence (80%, 82% and 81% for BNS1, BNS2 and BNS3, respectively). Conversely, the network presence values decrease after BNS3 to reach 64%, 62% and 41% for BNS4, BNS5 and BNS6, respectively.

It has been shown that k-mean clustering gives the most appropriate results for grouping together the topography maps of voltages related to EEG micro-state events as compared with other clustering approaches. This approach has also been adopted to identify functional connectivity states at resting times using fMRI. However, other algorithms could be assessed, such as that of the modified Hierarchical Ascendant Classification (HAC).

As for the measurement of functional connectivity, the PLV method offers high performance to detect inter-trial synchronization at each time slot. However, the PLV method requires a relatively large number of stimuli (148 in the present case for each subject) for accurate estimation. This method therefore cannot be easily applied to an activity in progress, such as for the analysis of the networks in resting states for example.

Although the connectivity of the EEG sources reduces the problem of field spread to a certain extent (compared with scalp EEG connectivity), it does not yet provide a perfect solution. The field spread effect is an open question. It is indeed one of the main challenges in the execution of the reverse EEG/MEG solution. In the context of connectivity, the main effect of field spread is represented by possible "artificial" correlations that may exist between very close sources.

Thus, in order to resolve the field spread effect, it was first of all decided to use the PLV method which has proved to reduce field spread. The second step is that of clustering or anatomical parcellation which consists in reconstructing the sources on a high spatial resolution cortex mesh and then computing the dynamic average of the sources located in the same regions of interest (ROI). The connectivity is then computed between these averaged sources. The same approach is used during the analysis of connectivity of the MEG sources. The advantage of this mean is that i) it increases the distance between the positions of the regions of interest (ROI) defined by their centre of mass and ii) reduces the "artificial" correlations of very close sources located in the same regions of interest (ROI).

Some approaches have been proposed recently to resolve source leakage, either by normalizing the operations for weighting the arcs by the distance between the nodes or by eliminating very close edges. Although these approaches offer certain advantages, it has been shown that, in most cases, they also eliminate "real" connections.

FIG. 4 illustrates a device such as a brain-imaging device capable of implementing a resource according to the present technique. According to one specific implementation, the different acts of the method are implemented by one or more software programs or computer programs 43 comprising software instructions that are to be executed by a processor 42 of an information-processing device, such as a terminal and being designed to command the execution of the different acts of the methods. An embodiment is therefore also aimed at providing a computer program 43, capable of being executed by a computer or by a data processor 42, this program comprising instructions to command the execution of the method as mentioned here above.

Although the present disclosure has been described with reference to one or more examples, workers skilled in the art will recognize that changes may be made in form and detail without departing from the scope of the disclosure and/or the appended claims.

The invention claimed is:

1. A method for determining a sequence of activation of a set of brain networks, in the course of a predetermined cognitive task, wherein the method comprises the following acts performed by an electronic device:
    obtaining at least one time series of data on encephalographic activities, according to a predetermined sampling value, said data on activities representing a signal captured on the cranial surface by a capture device, during execution of said predetermined cognitive task by at least one individual, the obtaining delivering a set comprising at least one measurements vector per sample of the time series;
    for each measurements vector, determining a connectivity between cortical sources, said cortical sources being obtained through measurements of a measurements vector, delivering a connectivity network; and
    grouping connectivity networks according to a resemblance parameter delivering a set of groups of grouped connectivity networks, each representing an activity of a given brain network at a given instant, wherein grouping comprises a statistic validation of said groups of connectivity networks obtained from substitution data, comprising a comparison of spatial distribution and temporal profiles of said groups of connectivity networks obtained in said grouping with groups of connectivity networks obtained from substitution data.

2. The method for determining according to claim 1, wherein the obtaining a time series comprises:
    a plurality of acts of obtaining a plurality of values of signals captured at the cranial surface of said at least one individual, said plurality of values representing a number of signal capture devices, said plurality of acts of obtaining these pluralities of values depending on a duration of said predetermined cognitive task and of said predetermined sampling;
    a plurality of acts of associating said value with a given cortical source, delivering said set comprising at least one source vector per sample.

3. The method for determining according to claim 2, wherein the number of signal capture devices is greater than 128.

4. The method for determining according to claim 1, wherein said sampling value ranges from 0.2 ms to 30 ms.

5. The method for determining according to claim 1, wherein said determining connectivity between cortical sources of a vector comprises:
- detecting sources from which the signals of said vector have come, said detecting implementing a weighted minimum norm estimation, delivering a source vector; and
- computing a functional connectivity between the previously detected sources, by using a method of phase synchronization, delivering a connectivity network for the source vector.

6. The method for determining according to claim 1, wherein said grouping connectivity networks according to a resemblance parameter comprises at least one iteration of the following acts:
- selecting a predetermined number K of networks from among the set of connectivity networks;
- computing, for each network among the number K of previously selected networks, a spatial correlation between this network and the set of connectivity networks;
- selecting the network for which the spatial correlation is the highest and allocating, to this network, the spatially closest networks.

7. An electronic device for determining a sequence of activation of a set of brain networks during a predetermined cognitive task, the electronic device comprising:
- a data processor; and
- a non-transitory computer-readable medium comprising instructions stored thereon, which when executed by the data processor configure the device to perform acts comprising:
  - obtaining at least one time series of data on encephalographic activities, according to a predetermined sampling value, said data on activity representing a signal captured on the cranial surface by at least one capture device during the execution of said predetermined cognitive task by at least one individual, wherein the obtaining delivers a set comprising at least one measurements vector per sample of the time series;
  - determining a connectivity between cortical sources for each measurement vector, said cortical sources being obtained from measurements of a measurement vector, delivering a connectivity network; and
  - grouping connectivity networks according to a resemblance parameter delivering a set of groups of grouped connectivity networks, each being representative, at a given instant, of an activity of a given brain network, wherein grouping comprises a statistic validation of said groups of connectivity networks obtained from substitution data, comprising a comparison of spatial distribution and temporal profiles of said groups of connectivity networks obtained in said grouping with groups of connectivity networks obtained from substitution data.

8. A non-transitory computer-readable medium comprising instructions stored thereon for performing a method of determining a sequence of activation of a set of brain networks, in the course of a predetermined cognitive task, when the instructions are executed by a data processor, wherein the method comprises:
- obtaining at least one time series of data on encephalographic activities, according to a predetermined sampling value, said data on activities representing a signal captured on the cranial surface by a capture device, during the execution of said predetermined cognitive task by at least one individual, the obtaining delivering a set comprising at least one measurements vector per sample of the time series;
- for each measurements vector, determining a connectivity between cortical sources, said cortical sources being obtained through measurements of a measurements vector, delivering a connectivity network; and
- grouping connectivity networks according to a resemblance parameter delivering a set of groups of grouped connectivity networks, each representing an activity of a given brain network at a given instant, wherein grouping comprises a statistic validation of said groups of connectivity networks obtained from substitution data, comprising a comparison of spatial distribution and temporal profiles of said groups of connectivity networks obtained in said grouping with groups of connectivity networks obtained from substitution data.

* * * * *